United States Patent [19]

Shapiro et al.

[11] 4,440,690

[45] Apr. 3, 1984

[54] PROCESS FOR THE SYNTHESIS OF 6-BROMO-17,21-DIHYDROXY 3,11,20-TRIOXO-1,4-PREGNADIENES 17,21-DIESTERS

[75] Inventors: Elliot L. Shapiro, Cedar Grove; Lawrence E. Finkenor, Wayne, both of N.J.

[73] Assignee: Schering Corporation, Kenilworth, N.J.

[21] Appl. No.: 453,844

[22] Filed: Dec. 27, 1982

[51] Int. Cl.$^3$ .............................................. C07J 5/00
[52] U.S. Cl. .................................................. 260/397.45
[58] Field of Search ............. 260/397.45, 397.2, 397.4

[56] References Cited

PUBLICATIONS

Djerassi et al., Journal American Chemical Soc. 72, (1950), pp. 4534–4540.

*Primary Examiner*—Elbert L. Roberts
*Attorney, Agent, or Firm*—Stephen I. Miller; Bruce M. Eisen; Gerald S. Rosen

[57] ABSTRACT

Disclosed is an improved process for the synthesis of 6-bromo-17,21-dihydroxy-3,11,20-trioxo-1,4,-pregnadienes 17,21-diesters. In particular, this invention relates to the conversion of 17,21-dihydroxy-3,11,20-trioxo-1,4-pregnadienes 17,21-diesters to 6-borom-17,21-dihyroxy-3,11,20-trioxo-1,4-pregnadienes-17-21-diesters via bromination under ionic conditions, e.g. bromine in acetic acid.

5 Claims, No Drawings

PROCESS FOR THE SYNTHESIS OF 6-BROMO-17,21-DIHYDROXY 3,11,20-TRIOXO-1,4-PREGNADIENES 17,21-DIESTERS

The present invention pertains to an improved process for the selective synthesis of 6-bromo-3,11,20-trioxo-1,4-pregnadienes. In particular, this invention relates to the conversion of 17,21-dihydroxy 3,11,20-trioxo-1,4-pregnadienes 17,21-diesters to 6-bromo-17,21-dihydroxy-3,11,20-trioxo-1,4-pregnadienes 17,21-diesters via bromination under ionic conditions, e.g. bromine in acetic acid. The 6-bromo-17,21-dihydroxy 3,11,20-trioxo-1,4-pregnadienes 17,21-diesters are useful intermediates in the synthesis of anti-inflammatory steroids, e.g. 7α-chloro-16α-methyl-1,4-pregnadiene-11β,17α,21-triol-3,20-dione 17,21-dipropionate.

Free radical bromination (Wolf-Ziegler reaction) is a known method for the preparation of 6-bromo-3,11,20-trioxo-1,4-pregnadienes and is described by Kaufmann et al, Journal American Chemical Society, 72, 4531 (1950). However, the Wolf-Ziegler is not a desirable reaction for the synthesis of 6-bromo steroids possessing a 21-propionate as a significant amount of unwanted bromination occurs at the methylene moiety of the propionate.

We have now surprisingly found that the synthesis of 6-bromo-17,21-dihydroxy-3,11,20-trioxo-1,4-pregnadienes 17,21-diesters may be accomplished selectively and in high yields by bromination under ionic conditions.

Ionic chlorination of 3-oxo-1,4-dienes to produce 3-oxo-1,2-dichloro-4-enes is described by Kirk and Petrow, J. Chem. Soc., 1334–1342 (1958).

Ionic bromination of Δ-4-androstene and 19-desmethyl Δ-4-androstene yielded the 2,6-dibromo analogues and is described by Fried and Edwards, *Organic Reactions in Steroid Chemistry*, volume I, pg. 284, (Van Nostrand Reinhold Co., NY., NY., 1972). In the same article, Fried and Edwards also reported that the yield of the ionic bromination dropped significantly (95% to 80–82%) when the 19-desmethyl Δ-4-androstene starting material was replaced by Δ-4-androstene.

In comparison to free radical bromination, and in view of Fried and Edwards, surprisingly and unexpectedly high yields of the 6-bromo-17,21-dihydroxy-3,11,20-trioxo-1,4-pregnadienes 17,21-diesters are selectively obtained by bromination under ionic conditions.

By the term, "selectively" and "selective" we mean that the bromination occurs predominately at the 6 position of the steroid moiety.

The present invention pertains to an improved process for the selective synthesis of a compound of the formula

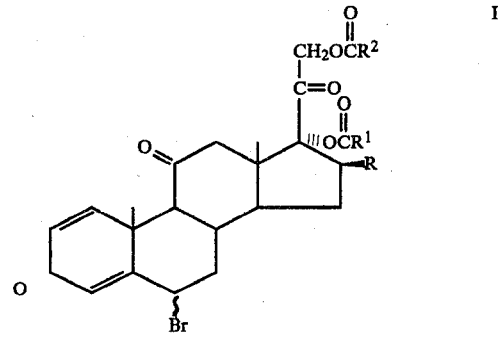

wherein R is hydrogen or lower alkyl; and $R^1$ and $R^2$ are independently selected from lower alkyl; which comprises reaction of a compound of the formula

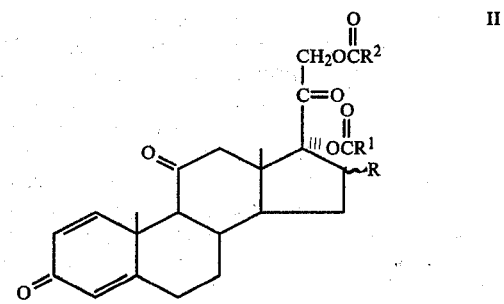

wherein R is hydrogen or lower alkyl; and $R^1$ and $R^2$ are independently selected from lower alkyl; with bromine in a solution of hydrogen bromide in acetic acid.

Preferably an inert organic solvent such as 1,4-dioxane, tetrahydrofuran and the like is added to the system as a diluent. Most preferably 1,4-dioxane is employed.

Preferably $R^1$ and $R^2$ are independently selected from methyl, ethyl, n-propyl and n-butyl.

Preferably R is hydrogen or methyl.

Most preferably, R is methyl, $R^1$ and $R^2$ are ethyl.

It is contemplated that other organic acids such as propionic acid, chloroacetic acid and the like may be employed in the reaction.

As used herein, the term "loweralkyl" refers to straight- and branched-chain alkyl groups having a total of from 1 to through 6 carbons and includes primary, secondary, and tertiary alkyl groups. Typical lower alkyls include, for example, methyl, ethyl, n-propyl, isopropyl, n-butyl, t-butyl, n-hexyl and the like.

DETAILED DESCRIPTION OF THE INVENTION

The process of the present invention is accomplished by reaction of a compound of the formula I wherein R, $R^1$ and $R^2$ are as defined above; with bromine in a solution of hydrogen bromide in acetic acid to give a compound of the formula II wherein R, $R^1$ and $R^2$ are as defined above.

The reaction is accomplished by first adding hydrogen bromide, approximately 20–30% by weight to starting compound II, to acetic acid. An inert organic solvent such as 1,4-dioxane, tetrahydrofuran and the like may be added to the acetic acid as a diluent. Preferably, the dilution is accomplished prior to the addition of hydrogen bromide. Most preferably, the reaction is accomplished by employing a solution of 25% by weight to II of hydrogen bromide in 6:4 dioxane:acetic acid. 1.0 to 1.2 equivalents to II, preferably 1.1 equivalents, of bromine is then added to this solution. Afterwards, the starting compound, II, is added to the system.

The reaction is generally conducted at from −15° C. to 35° C.; and preferably at from 18° C. to 25° C. Reaction pressure is not critical and for convenience the reaction is generally conducted at atmospheric pressure. The reaction is generally complete from within 5 minutes to 1 hour. The product, I, is then isolated by conventional procedures such as filtration, chromatography, distillation, extraction and the like.

6-bromo-17,21-dihydroxy-3,11,20-trioxo-1,4-pregnadiene 17,21-diesters are particularly useful intermediates in the synthesis of anti-inflammatory steroids. For instance, as described in U.S. Pat. No. 4,124,707, 6-bromo-17,21-dihydroxy-16α-methyl-1,4-pregnadiene-11β,17α,21-triol-3,20-dione 17,21-dipropionate may be readily converted to the corresponding 17,21-dihydroxy-16α-methyl-1,4,6-pregnatriene-11β,17α,21-triol-3,20-dione 17,21-dipropionate which in turn may be converted to known antiinflammatory steroids such as 7α-chloro-16α-methyl-1,4-pregnadiene-11β,17α,21-triol-3,20-dione 17,21-dipropionate.

A further understanding of the invention can be had in the following non-limiting Example, wherein, unless expressly stated to the contrary, all temperatures and temperature ranges refer to the centigrade system and the term "ambient" or "room temperature" refers to about 18° to 25° C. Furthermore, the stereochemistry of the substituents at the 6 and 16 positions may be either α; β or a mixture of α and β while the stereochemistry of the hydroxyl group at the 17 position is strictly α.

EXAMPLE 1

Preparation of 6-bromo-17,21-dihydroxy-16α-methylpregna-1,4-diene-3,11,20-trione 17,21-dipropionate Add 10 gm of 17,21-dihydroxy-16α-methylpregna-1,4-diene-3,11,20-trione 17,21-dipropionate to a mixture of 2.5 gm anhydrous hydrogen bromide gas in 100 ml of 6:4 1,4-dioxane:acetic acid. Dissolve 3.63 gm of bromine into 10 ml of acetic acid. Add the bromine in acetic acid to the reaction system. Stir the system at 18°–25° C. for 5 minutes. Immediately pour the reaction system into 1.1 l of a 1% sodium acetate solution at 0°–5° C. Isolate the product by filtration and wash the filtrate with water. Dry the product at 45° to a constant weight to give the title product.

What is claimed is:

1. A process for the selective synthesis of a compound of the formula:

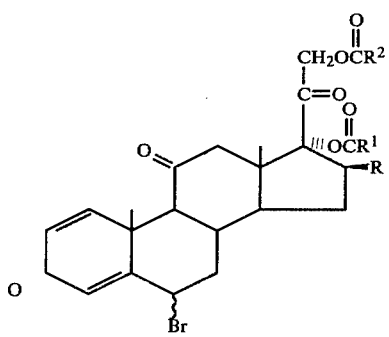

wherein R is hydrogen or lower alkyl; and $R^1$ and $R^2$ are independently selected from lower alkyl; which comprises reaction of a compound of the formula

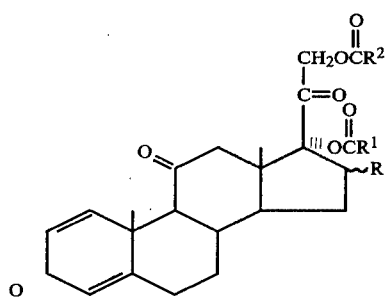

wherein R is hydrogen or lower alkyl; and $R^1$ and $R^2$ are independently selected from lower alkyl; with bromine in a solution of hydrogen bromide in acetic acid.

2. A process for the synthesis of a compound of the formula:

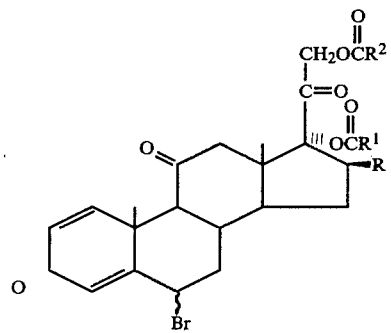

wherein R is hydrogen or lower alkyl; and $R^1$ and $R^2$ are independently selected from lower alkyl; which comprises reaction of a compound of the formula

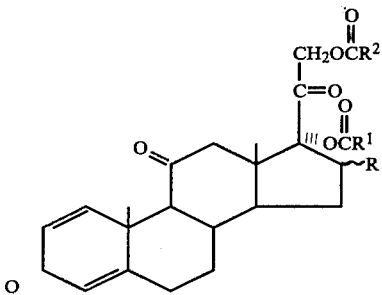

wherein R is hydrogen or lower alkyl; and $R^1$ and $R^2$ are independently selected from lower alkyl; with bromine in a solution of hydrogen bromide in acetic acid and dioxane.

3. The process of claim 2 wherein R is methyl and $R^1$ and $R^2$ are ethyl.

4. A process for the synthesis of 6-bromo-17,21-dihydroxy-16α-methyl-3,11,20-trioxo-1,4-pregnadiene 17,21-dipropionate which comprises reaction of 17,21-dihydroxy-16α-methyl-3,11,20-trioxo-1,4-pregnadiene 17,21-dipropionate with 1.0 to 1.2 equimolar amount of bromine and 25% by weight of hydrogen bromide in a solution of 6:4 dioxane:acetic acid at −15° C. to 35° C.

5. The process of claim 4 wherein the reaction is conducted at 18° C. to 25° C.

* * * * *

UNITED STATES PATENT AND TRADEMARK OFFICE
CERTIFICATE OF CORRECTION

PATENT NO. : 4,440,690

DATED : April 3, 1984

INVENTOR(S) : Elliot L. Shapiro and Lawrence B. Finkenor

It is certified that error appears in the above—identified patent and that said Letters Patent is hereby corrected as shown below:

The addition of a double bond at the 3 position of the formulae in column 2, lines 1 - 12, in column 3, lines 55-56 and in column 4, lines 5-16, lines 24-35 and lines 41-52.

The replacement of the solid line with a wiggly line at the 16 position of the formulae in column 2, lines 1-12, in column 3, lines 55-56 and in column 4, lines 24-35.

Signed and Sealed this

Sixteenth Day of October 1984

[SEAL]

Attest:

GERALD J. MOSSINGHOFF

Attesting Officer

Commissioner of Patents and Trademarks